United States Patent [19]

Leckband et al.

[11] Patent Number: 4,794,532
[45] Date of Patent: Dec. 27, 1988

[54] VIRTUAL ARRHYTHMIA SYSTEM

[75] Inventors: Ellen V. Leckband, Bedford; Larry L. Nielsen, Burlington, both of Mass.

[73] Assignee: Hewlett-Packard Company, Palo Alto, Calif.

[21] Appl. No.: 929,548

[22] Filed: Nov. 10, 1986

[51] Int. Cl.[4] .............................................. G06F 15/42
[52] U.S. Cl. ............................... 364/413.06; 128/709; 128/710
[58] Field of Search ............... 364/415, 417; 128/702, 128/709, 710

[56] References Cited

U.S. PATENT DOCUMENTS

| | | | |
|---|---|---|---|
| 3,925,762 | 12/1975 | Heitlinger | 340/870.09 |
| 4,051,522 | 9/1977 | Healy | 340/721 X |
| 4,090,505 | 5/1978 | Mortara | 364/417 |
| 4,216,462 | 8/1980 | McGrath | 340/870.11 X |
| 4,667,682 | 5/1987 | Ihlenfeld | 128/702 |

OTHER PUBLICATIONS

Schluter, "A Bedside Cardiac Arrhythmia Monitor", 3/1980, pp. 381–385.

V. N. Parde, "Bedside ECG Monitor Using a Microprocessor", 9/1985, pp. 487–492.

Primary Examiner—Jerry Smith
Assistant Examiner—Steven Kibby
Attorney, Agent, or Firm—Donald N. Timbie

[57] ABSTRACT

A patient arrhythmia monitoring system having a plurality of bedside stations that can derive physiological data for a patient coupled thereto, a central station, a bus for providing communication between said bedside stations and said central station. A processor is provided for analyzing the data from each station. Criteria for the indication of an alarm for a bedside station can be set at that station and at the central station. When an alarm is indicated for a bedside station, the data causing it can be viewed at that station as well as at the central station. Selected alarm data is temporarily stored by said processor in such manner that the data for any bedside station can be recalled at the bedside station from which it came and at the central station, A printer is provided for printing the selected alarm data for any bedside station on a separate page.

2 Claims, 10 Drawing Sheets

VIRTUAL ARRHYTHMIA SYSTEM

BACKGROUND OF THE INVENTION

In recent years the pressure to cut costs in intensive care and coronary care units has lead to the use of monitoring apparatus having bedside units for deriving physiological data for each patient and means for displaying that data at the bedside where it was derived and at a central station. It has also been possible to view data at one bedside that is derived at another. If it were necessary to analyze the real time data for each patient all of the time, the number of nurses would not be reduced significantly so that it has been customary to provide such monitoring systems with computers or microprocessors that are programmed with algorithms for analyzing the data for each patient to render a "yellow" alert when a situation of some concern but which is not life threatening exists and a "red" alert when a situation exists that may be life threatening. Past practice has been to sequentially record on paper at the central station all of the data occurring during either of these alerts so that it can be subsequently reviewed by a physician. Because the algorithms are usually designed to give alerts in borderline situations, the amount of data that must be reviewed by the physician can be excessive and much of it is redundant. Furthermore, if a physician or other clinician is at the bedside and desires past data, it is necessary to obtain the paper recordings. This requires a lot of pasting and cutting in order that the strips for a given patient may be separated from the others. A significant inconvenience of prior monitoring systems is that the control of what data is to be displayed and the condition under which it is to be displayed is at the central station or the bedside.

BRIEF SUMMARY OF THE INVENTION

In accordance with this invention a monitoring system is provided in which past data acquired during yellow and red alerts is stored electronically so that it can be quickly viewed at bedside rather than having to wait for the printed recordings to be made available. Furthermore, controls are provided at the bedside so that the past data can be edited. After editing, the desired data is printed on paper. The amount of paper used and the labor in cutting and pasting is greatly reduced. Furthermore, inasmuch as the editing for any patient can be finished before any printing is done, all significant data for a given patient can be printed on a separate piece of paper that can be placed on his file for a review by a physician.

DETAILED DESCRIPTION OF THE INVENTION

Figure 1:
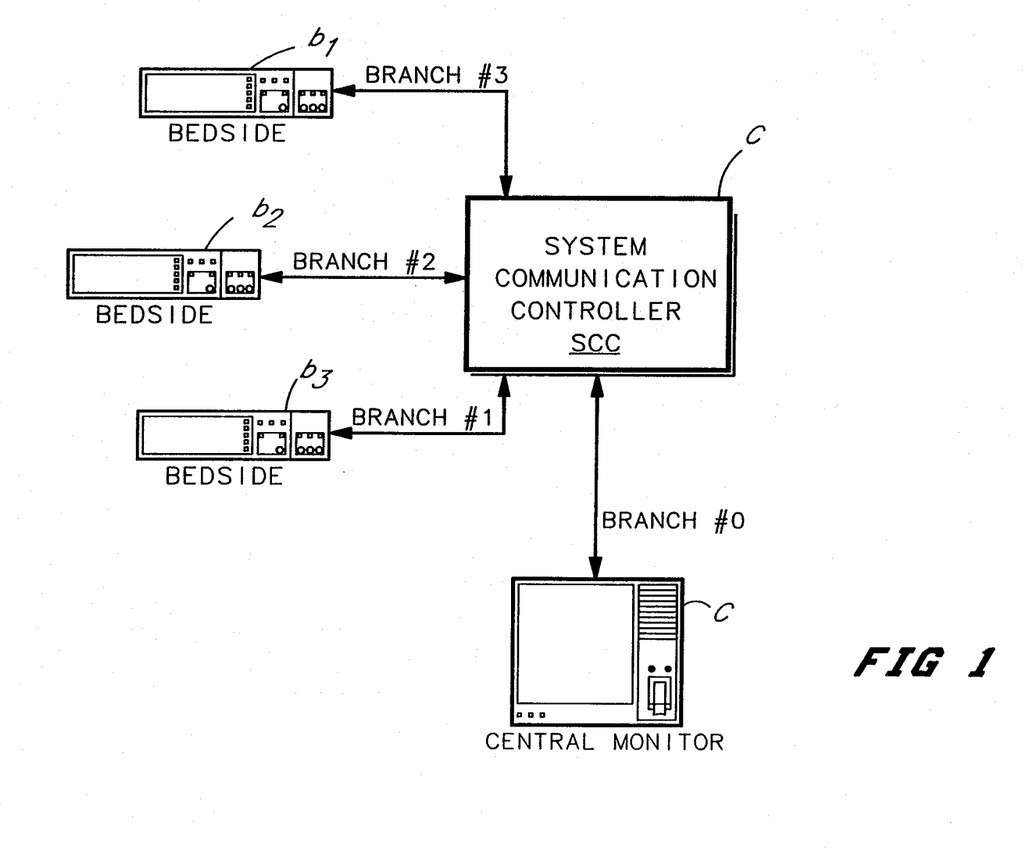
FIG. 1 illustrates the interconnection of a central station with bedside stations by a bus having a star topography.

FIG. 1 illustrates one configuration that a system incorporating this invention may have. Three beside stations $b_1$, $b_2$ and $b_3$ are shown at the ends of respective arms from a system communication controller SCC, and a central station C is shown as being connected to the end of another arm. Thus the bussing system interconnecting $b_1$, $b_2$, $b_3$ and C has a star topography in which the system controller SCC may be the Hewlett Packard Controller 78581A. In this system all stations are allowed to transmit to the SCC during sequential intervals. During these intervals the SCC transmits what it receives from one bedside station to all the others. It will be understood by those skilled in the art that a bus system having different topography could be used.

Figure 2:
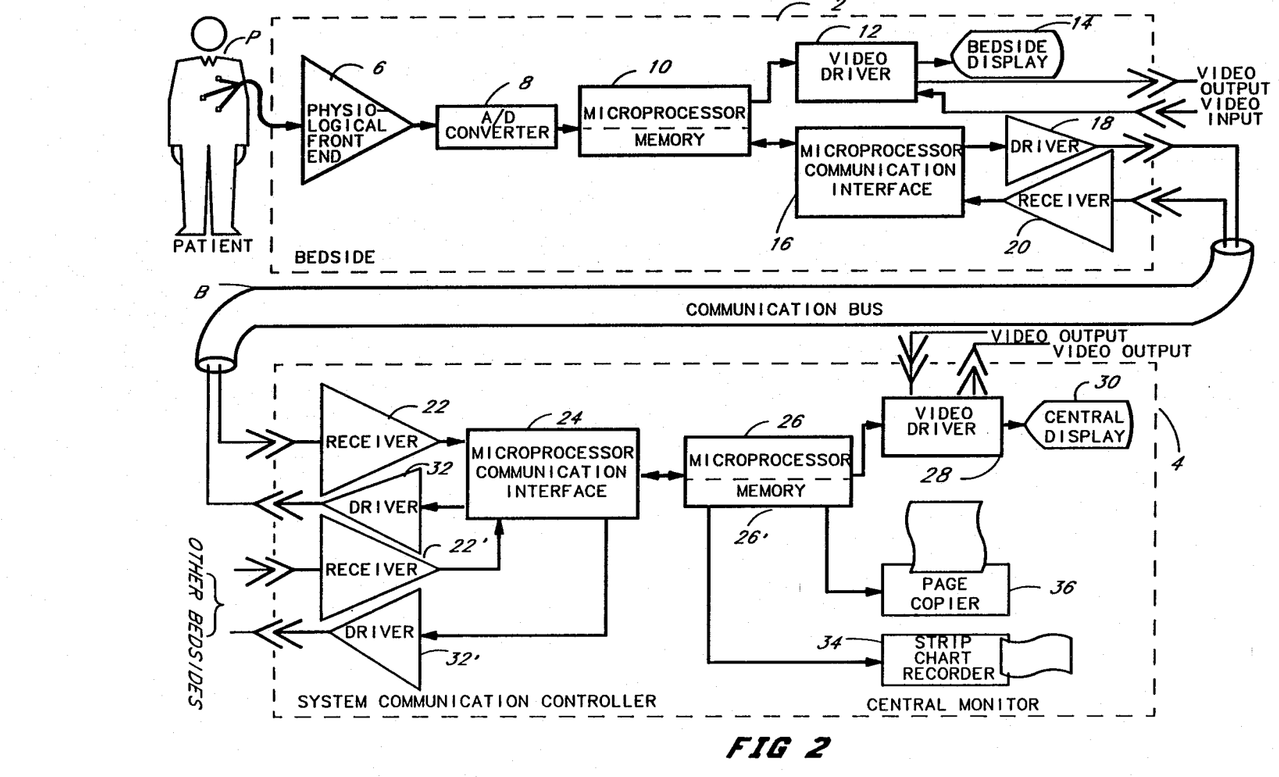
FIG. 2 is a block diagram of bedside and central stations used in a system incorporating this invention.

FIG. 2 shows in block diagram form the major functional components of a bedside station 2 contained within a dashed rectangle and of a central station 4 contained within a separate dashed rectangle. A bus B provides communication between the stations.

In the bedside station 2 a means 6 is coupled to a patient P so as to derive signals representing physiological data such as EKG's and variation in blood pressure. These signals are converted into digital form by an A/D converter 8 before being applied to a microprocessor 10 that controls a drive circuit 12 for a bedside display 14. The microprocessor 10 also furnishes signals to another microprocessor 16 that interfaces with the bus B so as to transmit signals to it via a driver 18 and receive signals from it via a receiver 20. In the central station 4 a receiver 22 transfers signals placed on the bus B by the bedside stations to a microprocessor 24 that serves as an interface with the bus B and supplies the signals to a microprocessor 26 that prepares them for application to a video driver 28 that drives a central station display 30. The microprocessor 26 causes the signals from each of the bedside stations to appear at respectively different windows on the display 30.

Alternatively, video signals representing the physiological data can be sent via wires directly from the video driver 12 in a bedside station to the video driver 28 in the central station 4 and vica versa.

Either the microprocessor 10 at a bedside station or the microprocessor 26 in the central station can be programmed in well known ways to determine whether the data from a particular bedside warrants the assertion of a yellow or red alarm. If the determination is made by the microprocessor 10, an indication of the alarm is presented on the bedside display 14 and the central station display 30 in the same manner that other information is presented thereon, but if the determination is made by the microprocessor 26, it is presented to the bus interface microprocessor 24 and placed on the bus B via a driver 32. From the bus B it goes by way of the receiver 20 of the bedside station involved to the interface microprocessor 16, to the microprocessor 10 and from there to the display 14 via the video driver 12. It is to be understood that all messages for or from a particular bedside station are coded for that bedside station.

When either type of alarm occurs, the microprocessor 26 in the central station 4 stores the data causing the alarm in a memory 26'. Before printing the data with a strip chart recorder 34 or a page copier 36, it is edited by a nurse/monitor technician so as to eliminate redundant data as well as data that does not warrant an alarm.

One of the advantages of this invention is that the full review and editing can be done at the bedside station or the central station. Thus when a physician wants to review the patient's status, he need only consider pertinent data. Other bedside stations can be coupled to the microprocessor 24 by other receivers and drivers such as 22' and 32'.

Reference is now made to the frames shown in FIG. 3. The frame $F_1$ can only appear on the display of the central station but all of the others can appear on the displays of both bedside stations and the central station when they are called up. If arrhythmia analysis is to be performed by the microprocessor 26, an arrythmia function key $K_4$ that is in all stations is depressed. The next step is to designate the bedside stations for which the arrythmia analysis is to be performed. This is done by the soft keys $K_1$ and $K_2$ in the frame $F_1$ that are respectively for previous bed and next bed which move a reverse background band 38 to the bed selected. Previous to the depression of assignment key $K_3$, the frame $F_2$ will appear at all stations, but as soon as $K_3$ is depressed, an arrhythmia menu frame $F_3$ appears at the central station and at those bedside stations that have been selected by $F_1$ for arrhythmia monitoring. Arrhythmia monitoring can also be placed in operation for a particular bedside station by $K_4$.

When $K_3$ or $K_4$ are depressed, the learning process of the arrhythmia analysis algorithm of the microprocessor 26 commences and a frame $F_4$ comes up at all stations. It is important that the key $K_5$ be operated so as to indicate whether or not the patient at a particular bedside station, i.e. the one where the reverse background 38 appears, has a pacer or not. If it is desired to change limits of an alarm, e.g. the maximum and minimum pulse rates, $K_6$ is depressed and causes $F_5$ to appear at the station where the technician is located. $K_7$ and $K_8$ can then be depressed so as to respectively increase and decrease the limits. If conditions for inhibiting an alarm are desired, $K_9$ is depressed so as to bring $F_6$ up for view at the station where the technician is located. $F_6$ can also be brought up for view by depression of $K_{10}$ or of $F_4$. The arrhythmia menu frame $F_3$ can have control if $K_{11}$ of $F_4$ is depressed.

Figure 3A:
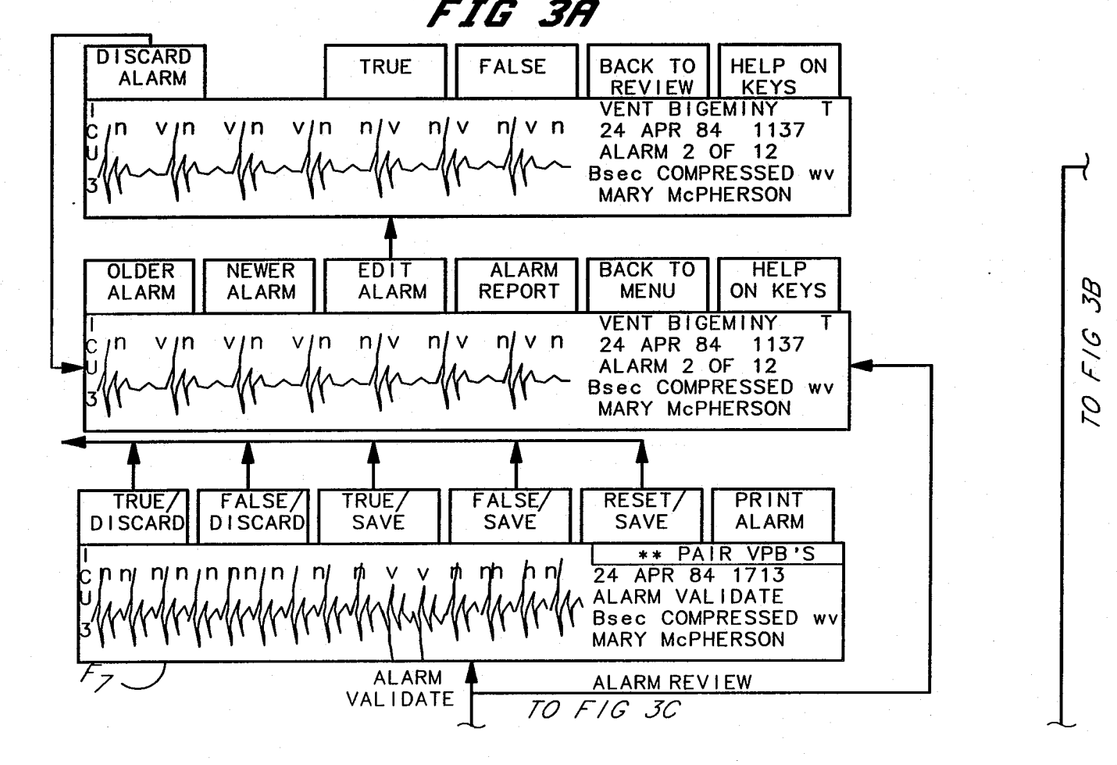
FIGS. 3A–3D illustrate the various frames that can come up on the screen of a central and bedside stations.
Figure 3B:
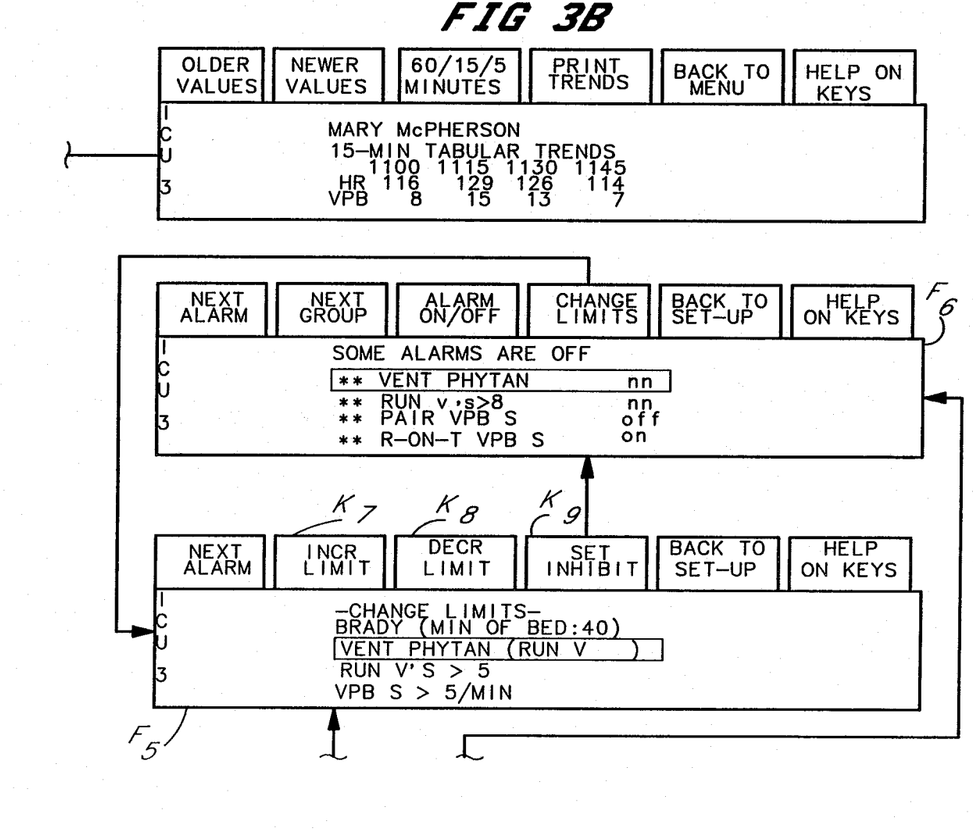
Figure 3C:
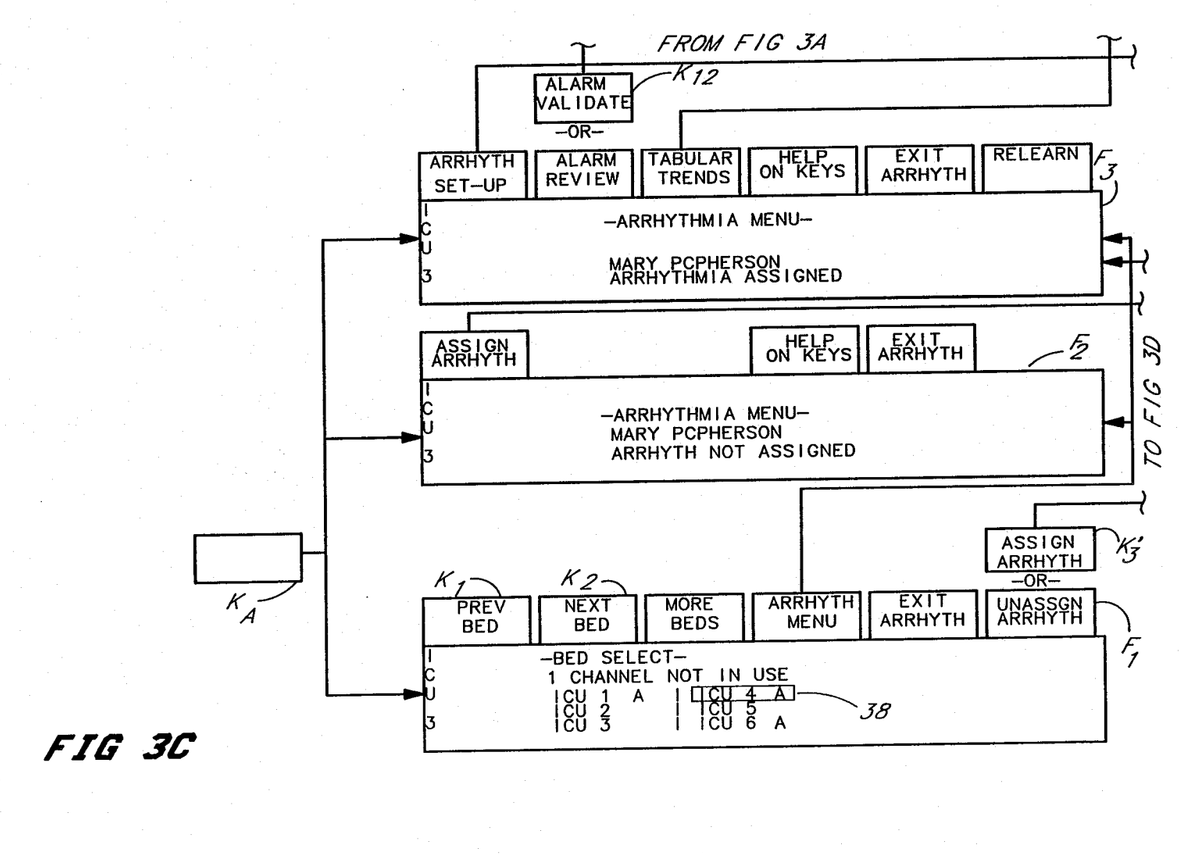
Figure 3D:
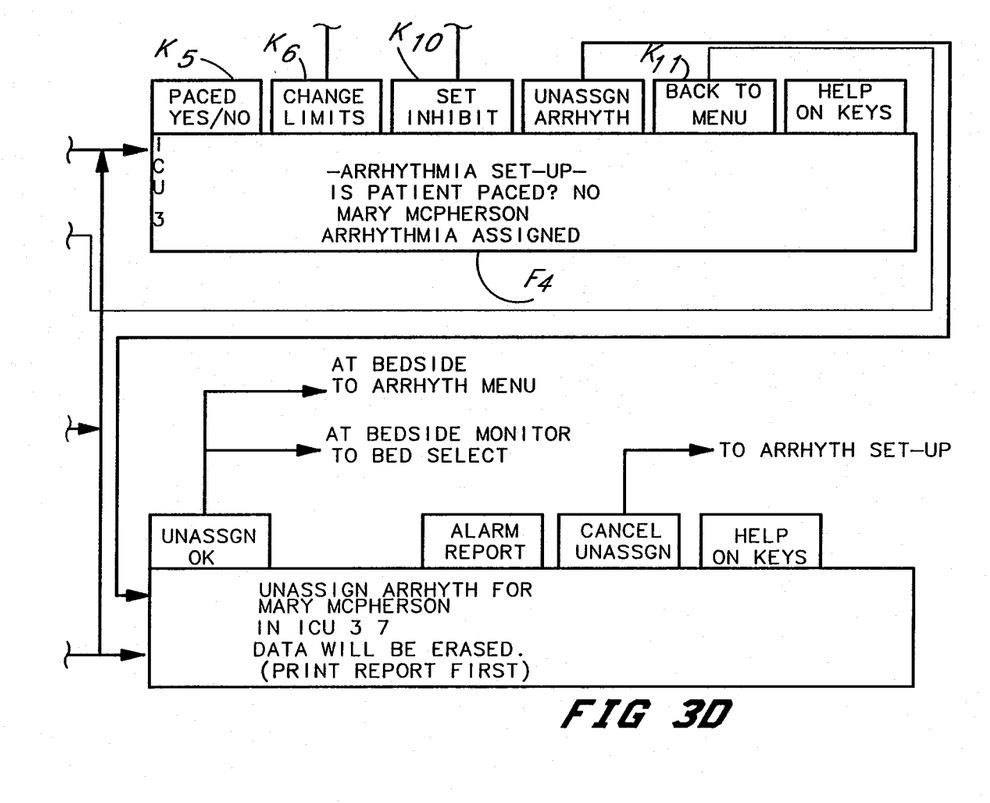
Figure 4:
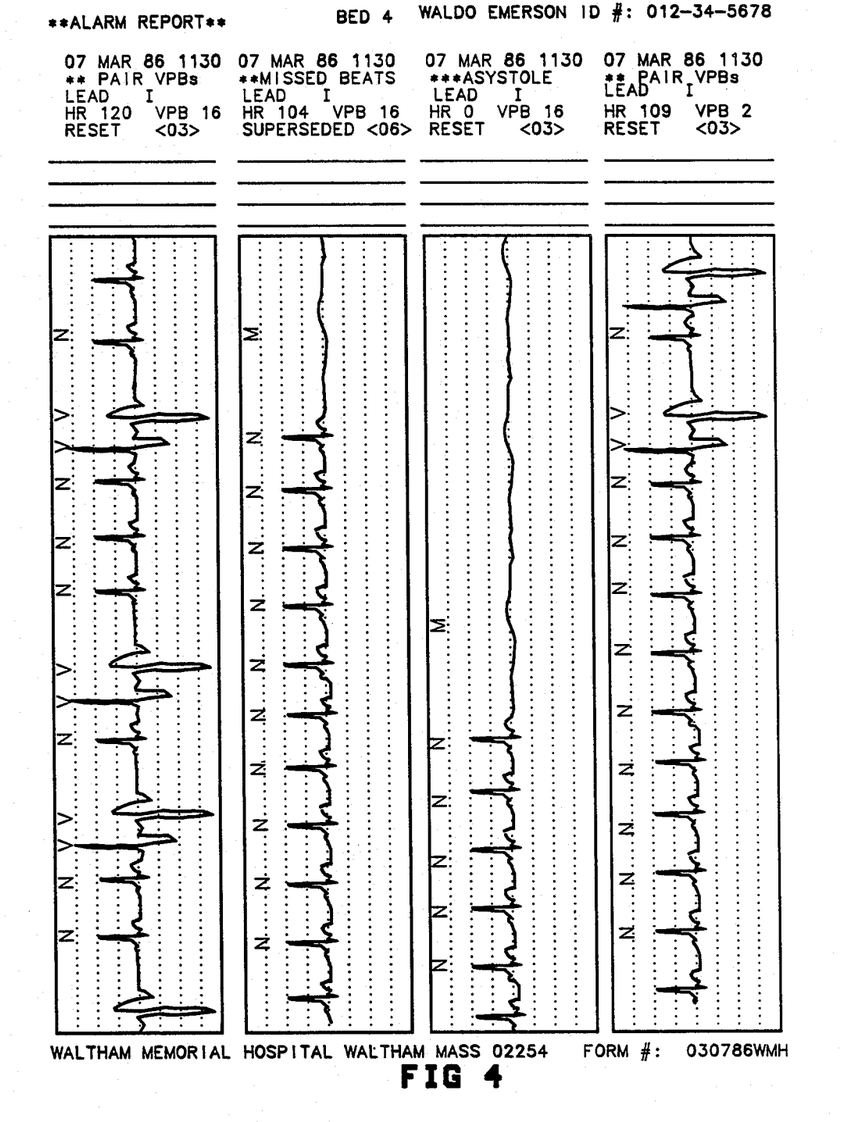
FIG. 4 illustrates an edited printed record produced in accordance with the invention.

Although not shown, the occurrence of any alarm for a patient is indicated by the appearance of a frame $F_7$ at his bedside unit and also at the central station. Alternatively, if $F_7$ does not come up automatically because the user is using the display for other purposes and it is desired to see if the alarm is vaid, $K_{12}$ of $F_3$ is depressed so that $F_7$ appears at the bedside involved. $F_7$ includes a number of EKG's including those that caused the alarm. After reviewing them, the technician can, as indicated by various keys on $F_7$, save or discard the EKG's whether they are considered to be valid or not. If they are saved, they will be recorded in the temporary memory 26'. At a later time, say when the physician comes in at the end of the day, all of the EKG's that were stored in 26' for the various alarms can be presented at bedsides involved or at the central station and/or printed copies provided by the page copier 36 may be examined. An example of a page is shown in FIG. 4.

Figure 5A:
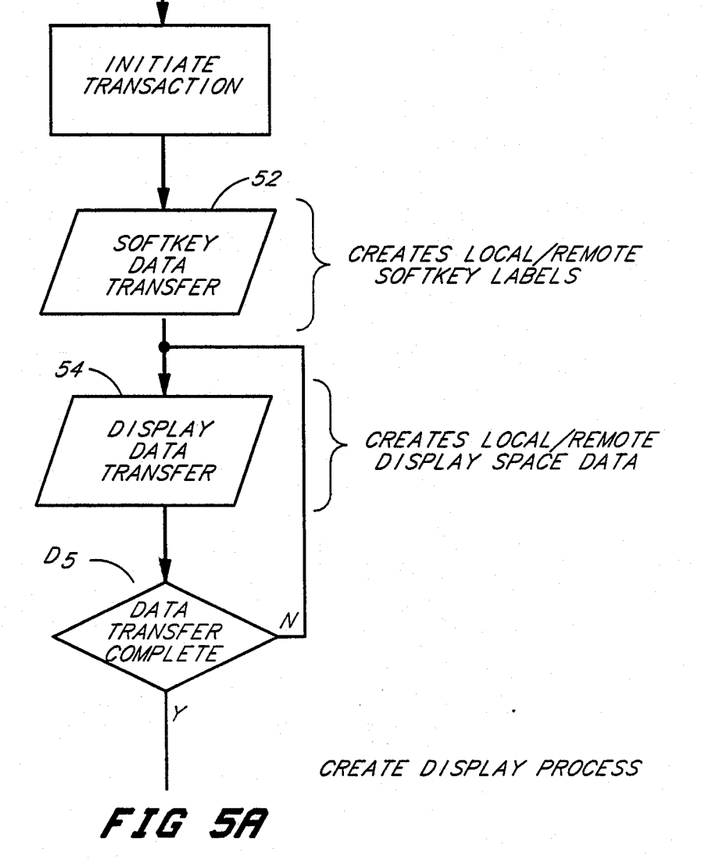
FIG. 5A is a flow chart of one block in FIG. 2, and FIGS. 5B and 5C are flow charts illustrating the operation of a system incorporating the invention.
Figure 5B:
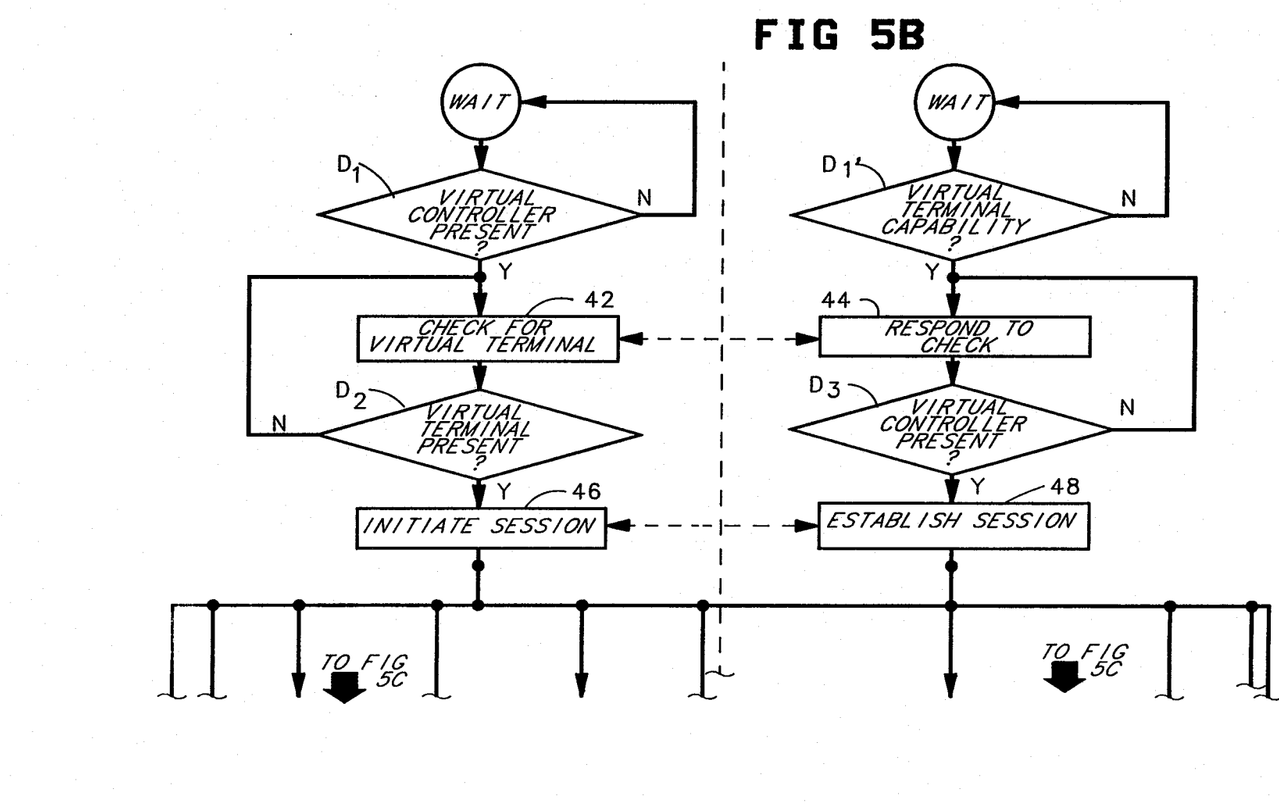
Figure 5C:
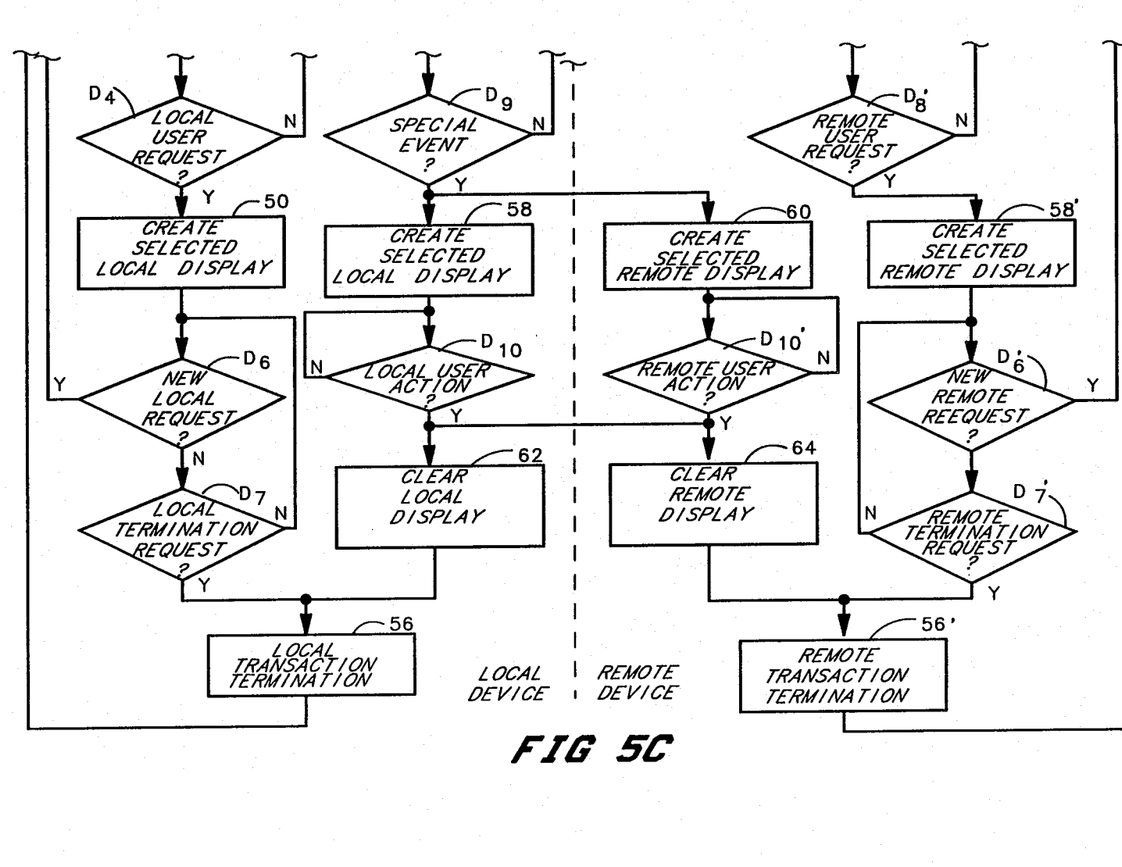

Reference is now made to the flow chart of FIGS. 5 and $5_A$ for a more detailed explanation of certain portions of the operation of a system incorporating the invention. The left side relates to the operation of the processor 26 of a central station and the right side relates to the operation of the microprocessor 10 of a bedside station.

Initialization of the system is achieved as follows. A decision block $D_1$ in the central station determines whether a controller C is present and at the same time a decision block D' in each bedside station determines whether its station is ready for operation. A block 42 in the central station checks with a block 44 to see if a bedside station is on the bus and is ready for operation. $D_2$ at the central station determines whether the answer received by 42 is affirmative. If not, it goes into a loop that awaits an affirmative reply. If so, it reaches a block 46 to respond to the depression of $K_A$ of FIG. 3 that initiates the arrhythmia procedure. After a decision block $D_3$ determines that a controller C is present, it reaches a block 48 so that the arrhythmia procedure may be carried out.

If the arrhythmia procedure is initiated by depression of a soft key $K_A$ at the central station, a decision block $D_4$ indicates this fact and a block 50 carries out the procedures indicated in FIG. $5_A$ in which a block 52 creates the proper soft key labels.

In this case it will be those of the bed selection frame $F_1$. A block 54 then creates the appropriate spacing data, and a decision block $D_5$ checks to see if all the required data for labels and space is complete. If it is, the block 50 creates the display of the frame $F_1$ at the central station. A decision block $D_6$ checks to see if a new request has been received. An example would be the selection of a bedside station by depression of keys $K_1$ or $K_2$ in $F_1$. This would require a menu frame $F_3$ to be added by the same process that has just been described to create $F_1$. If no new request has been received, $F_1$ remains in the display, and $D_7$ checks to see if a hard key has been depressed indicating that the arrhythmia process is to be terminated. If not, the procedure goes back to the input of $D_6$. If so, a block 56 sets up a standard display for the central station that remains until key $K_A$ is depressed.

If the soft key $K_A$ at a bedside station is depressed, a decision block $D_8$ indicates this fact, and a block 58 operates as described in connection with FIG. $5_A$ to display the arrhythmia menu frame $F_3$ at that bedside station and the central station. Decision blocks $D_6'$, $D_7'$ and 56' operate as the blocks $D_6$, $D_7$ and 56 respectively.

If a special condition such as a yellow or red alert should occur, the central station C is informed and a decision block $D_9$ indicates this condition. In response thereto blocks 58 and 60 respectively create a central station display and a display for the bedside station involved. Decision blocks $D_{10}$ and $D_{10}'$ then check to see if action such as the depression of the alarm validate key has been taken at either the central station or the bedside station involved. If not, the alarm remains, but if so, blocks 62 and 64 respectively clear the alarm indication from the central station and the bedside station from which the alarm emanated. The arrhythmia procedures in the central station and the bedside station are then respectively terminated by the blocks 56 and 56'. The procedures can be resumed by depressing any soft key $K_A$.

We claim:

1. An arrhythmia monitoring system comprising:
    at least one beside station that provides signals representing physiological data including waveforms when suitably coupled to a patient,
    a central station, means for providing communication between each bedside station and said central station, means coupled to a bedside station for analyzing physiological data provided thereby, means at each bedside station for setting conditions for the assertion of an alarm for that bedside station, means at said central station for setting conditions for the assertion of an alarm at any bedside station, alarm means coupled to each bedside station for providing an alarm signal at the bedside station and at said central station when the alarm conditions for said bedside station are met, storage means responsive to an alarm signal for saving physiological waveform data causing said alarm, means coupled to said storage means for displaying the physiological data causing a current alarm at the bedside station from whence the physiological data came, means coupled to said storage means for displaying the physiological data causing a current alarm at said central station, means at each bedside station and at said central station for eliminating at either station displayed physiological data causing the current alarm from said storage means, and means for recording physiological data from current alarms that has not been eliminated from said storage means.

2. An arrhythmia monitoring system as set forth in claim 1 further comprising:

means coupled to said storage means for retrieving from said storage means and displaying in sequence at a bedside station and at said central station a plurality of stored physiological waveform data caused by previous alarms that have not been eliminated for any bedside station, and means at each bedside station and at said central station for eliminating selected physiological data then displayed from said storage means, and means for recording physiological data not eliminated.

* * * * *